United States Patent
Novak et al.

(12)

(10) Patent No.: US 6,171,265 B1
(45) Date of Patent: Jan. 9, 2001

(54) HANDPIECE FOR USE WITH A MULTIFUNCTIONAL OPERATING ENDOSCOPIC INSTRUMENT

(75) Inventors: Pavel Novak, Schaffhausen; Beat Krattiger, Beringen; Klaus Irion, Liptingen, all of (CH); Frank Gminder, Trossingen (DE); Rudolf Henes, Schaffhausen (CH)

(73) Assignee: Storz Endoskop GmbH (CH)

( * ) Notice: Under 35 U.S.C. 154(b), the term of this patent shall be extended for 0 days.

(21) Appl. No.: 09/142,629

(22) PCT Filed: Jan. 7, 1998

(86) PCT No.: PCT/DE98/00041

§ 371 Date: Nov. 30, 1998

§ 102(e) Date: Nov. 30, 1998

(87) PCT Pub. No.: WO98/30155

PCT Pub. Date: Jul. 16, 1998

(30) Foreign Application Priority Data

Jan. 7, 1997 (DE) ............................ 197 00 270

(51) Int. Cl.⁷ .................................. A61B 17/30
(52) U.S. Cl. .................. 601/2; 606/39; 606/40; 606/41; 606/169; 607/101
(58) Field of Search ............... 607/101; 601/2–4; 606/32–41, 169; 604/22

(56) References Cited

U.S. PATENT DOCUMENTS

| | | |
|---|---|---|
| 3,433,226 | 3/1969 | Boyd . |
| 4,184,510 * | 1/1980 | Murry et al. ................ 137/565 |
| 5,047,043 * | 9/1991 | Kubota et al. ............... 606/169 |
| 5,312,329 | 5/1994 | Beaty et al. . |
| 5,391,144 | 2/1995 | Sakurai et al. . |
| 5,433,702 * | 7/1995 | Zelman et al. ............... 604/22 |
| 5,507,738 | 4/1996 | Ciervo . |
| 5,626,560 * | 5/1997 | Soring ......................... 604/22 |
| 5,776,092 * | 7/1998 | Farin et al. ................... 604/22 |
| 5,836,897 * | 11/1998 | Sakurai et al. ............... 601/2 |
| 5,871,493 * | 2/1999 | Sjostrom et al. ............. 606/180 |

FOREIGN PATENT DOCUMENTS

| | | |
|---|---|---|
| WO 91/07917 | 6/1991 | (WO) . |
| WO 93/16646 | 2/1993 | (WO) . |
| WO 95/10233 | 4/1995 | (WO) . |

* cited by examiner

*Primary Examiner*—Linda C. M. Dvorak
*Assistant Examiner*—David M. Ruddy
(74) *Attorney, Agent, or Firm*—St. Onge Steward Johnston & Reens LLC

(57) ABSTRACT

A handpiece is disclosed for a multifunctional instrument for endoscopic surgery. The handpiece comprises a case; a connector disposed on the case and adapted to be connected to connecting lines such as electrical lines, liquid supply and discharge lines, and the like; at least one ultrasonic transducer arranged in the case; an ultrasonic sonotrode transmitting the ultrasonic energy; and at least one switch for controlling functions of the handpiece. The handpiece is characterized by, among other things, the provision that the sonotrode includes a long and thin probe section with a duct composed of several segments which are welded to each other.

36 Claims, 4 Drawing Sheets

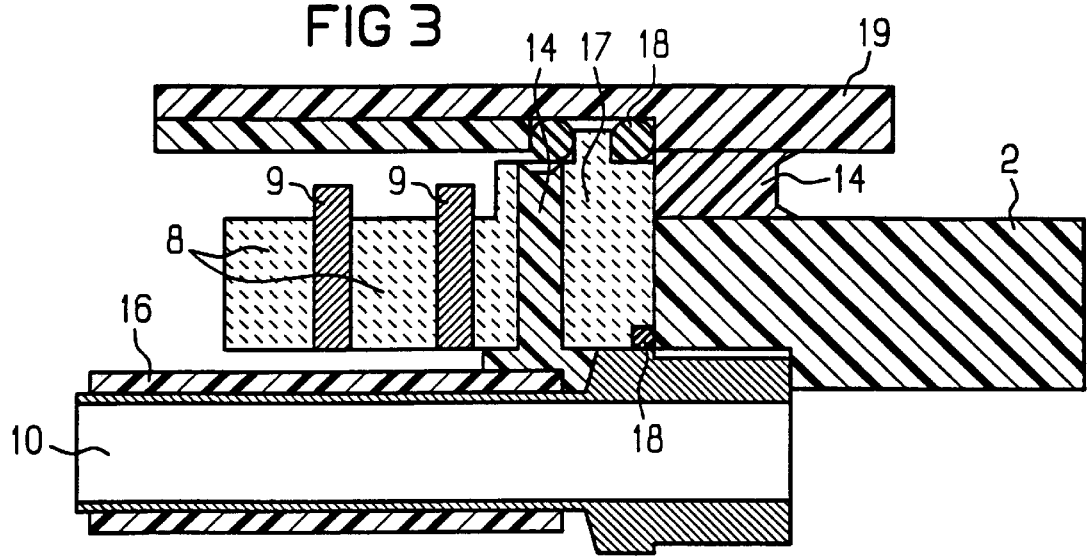
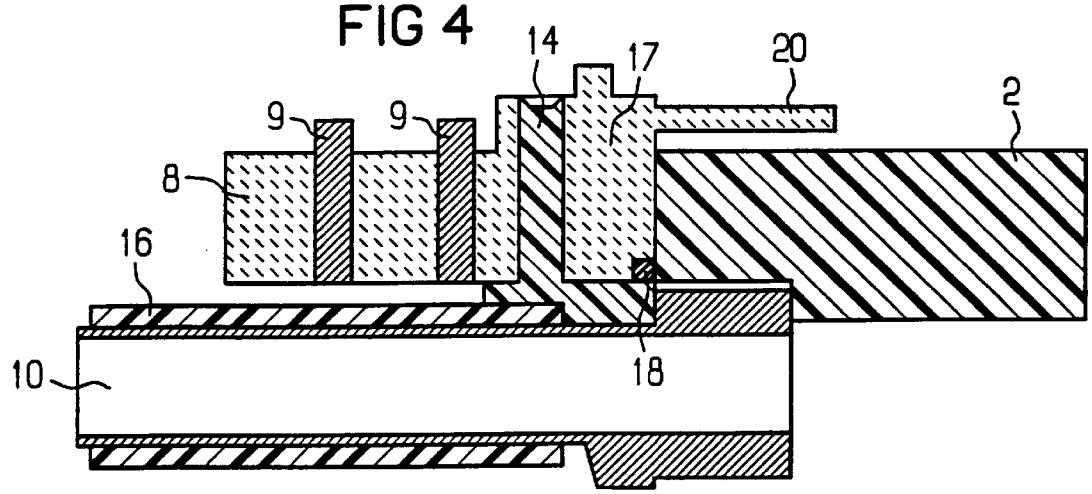

HANDPIECE FOR USE WITH A MULTIFUNCTIONAL OPERATING ENDOSCOPIC INSTRUMENT

FIELD OF THE INVENTION

The invention relates to a handpiece for a multifunctional instrument for endoscopic surgery, comprising a sonotrode for ultrasonic applications, in accordance with the introductory clause of Patent claim 1.

PRIOR ART

The wording of the introductory clause of the independent patent claims starts out, for instance, from the U.S. Pat. No. 5,391,144, which discloses various devices for ultrasonic treatment, or from the document WO-A-91/07917.

These references disclose handpieces for multifunctional devices for endoscopic surgery, which comprise a case, port means disposed on the case and adapted for connection to connecting lines such as electrical lines, lines for supply and discharge of liquids, etc., at least one ultrasonic transducer mounted in the case, one ultrasonic sonotrode for transmitting the ultrasonic energy to the distal end, and at least one switching means for control of the handpiece functions.

As far as the structure and the mode of operation of a sonotrode is concerned, reference is made specifically to the document WO-A-91/07917 to the extent to which it is assumed to be known within the scope of the present application.

As far as other aspects are concerned reference is made to the prior art documents identified above and mentioned in the following, as far as the explanation of all the terms is concerned which are not described here in details.

From the U.S. Pat. No. 5,391,144 instruments have become known which present the following features:
endoscopic application,
ultrasonic function,
high-frequency coagulation,
suction function,
irrigation and flushing
several ports in the rear zone of the handpiece,
switch on the handpiece, and
vapour sterilisability.

A similar device is described in the U.S. Pat. No. 5,312,329. In that ultrasonic and electro-surgical handpiece switches are mounted on the handpiece and provided with a separate supply line.

The devices known from the U.S. Pat. Nos. 5,391,144 and 5,312,329 present, however, a number of disadvantages:

For instance, switches are mounted on an existing handpiece or clamped on the outside of the case with a separate supply line. The switches used there present the following disadvantages:
The surgeon is disturbed by the switch mounted on the case and by the separate supply line. Moreover, the separate supply line is frequently damaged in application.
When switches are integrated often a cable lead-in is provided which involves an expenditure in terms of structure and which is a leak risk in autoclaving. For this reason it were desirable to avoid lead-in penetrations as far as possible.
When high frequency is activated (commonly at 5000 Vpp and 500 kHz) there is a breakdown or puncture risk. When common high-frequency wires and further wires are provided in a single cable the further wires are equally subjected to a high-frequency potential on account of capacitive coupling. It is necessary for this reason to insulate switches reliably from high frequencies from the outside. Even though this is feasible with a suitable structure comparatively big and bulky switches ought to be employed as a matter of fact. Small, less bulky switches such as foil push-buttons mounted on the envelope are not suitable for application in prior art.
For each function to be performed with the surgical device a separate line each is required for transmission and control.

Moreover, the devices known from the U.S. Pat. Nos. 5,312,329 and 5,391,144 display an insufficient insulation between the high-frequency and the ultrasonic supply in the handpiece, if an insulation is provided at all, so that high-frequency cross-talk to the ultrasonic supply will inevitably occur in the handpiece.

As a result even a high-frequency transmission to the ultrasonic generator may occur, which involves the risk of damage to the generator.

Another disadvantage of the describes described in the above-identified documents is the fact that a vibration-compatible design of the case and/or the sonotrode has not been considered.

BRIEF DESCRIPTION OF THE INVENTION

The present invention is based on the problem of defining a compact handpiece which is safe for the user and for the patient treated, which avoids the disadvantages of prior art and is easy to handle and yet stable.

The invention is moreover based on the problem of defining a handpiece for a surgical instrument which is functionally operable over a sufficient period despite the simultaneous integration of the ultrasonic function and the high-frequency application in one handpiece.

Another problem consists in the definition of a sonotrode which is simple to manufacture and presents a long service life.

Inventive solutions to these problems are defined in the independent claims. Improvements of the invention are the subject matter of the dependent claims.

The service life of the known sonotrodes is comparatively short, specifically in the case of long probe elements, because they are normally made of steel wire.

Even though the use of titanium or titanium alloys as probe material could be remedial the production of passages in such materials is possible only by boring, however. Deep-drilling with an acceptable reject rate is possible only up to roughly 200 to 300 mm.

In an approach to provide yet long probe elements a sonotrode is employed in accordance with the invention which comprises a long and thin probe section with a passage consisting of several segments welded together. The weld points may be located in particular in the antinodes of the ultrasonic wave. With this provision it is possible to produce probes of titanium or titanium alloys such as Ti6A14V where the passage diameter amounts to roughly 2 mm, the thickness of the probe section is less than 4 mm, and the length is more than 30 cm. The bored tubular segments are preferably formed or faced in such a way that they may be self-centred and welded.

The probe may specifically present a bulge which is welded on the probe section and screwed to the case. Regarding more details of the design reference is made to the document WO-A-91/07917 identified by way of introduction.

It is moreover expedient to probe a single connecting means and to mount all handpiece ports of the connecting lines in this single connecting means. A handpiece presenting these features saves additional cables outside the handpiece. All the ports are connected to the single connecting means which is disposed on one end of the handpiece or the case, respectively.

All the connecting lines which are of a design other than one-way lines—one-way lines are typically fluid lines—are expediently inserted into a cable sheath. This provision allows for a particularly simple handling of the handpiece.

Piezo transducers may preferably be used as ultrasonic transducers. With the inertial mass of prior art piezo transducers being normally connected to the electrical mass, it is common to use an ever number of piezo disks and hence an odd number of electrode surfaces.

For a minimisation of the current derived from the patient, by contrast, all the piezo disks should be expediently insulated from the inertial mass. With an even number of electrode surfaces, i.e. with the same number of positive and negative surfaces the positive and negative currents are substantially compensated, which result in a capacitive coupling with the inertial mass and may therefore arrive at the patient by contact.

It is moreover expedient to provide the ultrasonic generator with a floating symmetrical output so as to achieve that the currents which are capacitively coupled to the patient on account of the even number of electrode surfaces for reasons of symmetry will balance each other and form a minimum derivation current.

In another preferred embodiment the switching means includes at least one switching sensor and at least one actuator element which does not include any part which may be mechanically contacted with the switching sensor directly. In particular, this design does not establish an electrical connection so that high-frequency coupling will be avoided substantially as early as between the switch and the actuator element.

In accordance with the invention it has been found, as a matter of fact, that the disadvantages which occurred in prior art may be avoided by the provision that a switching function is transmitted through the case wall by remote control, e.g. magnetically, inductively, electromagnetically, optically and/or acoustically.

It is possible, for instance, to dispose a magnet in the mobile actuator element, outside the case or with integration in the case wall, which magnet switches a reed contact or a Hall probe, for instance, inside the hermetically tight case for the ultrasonic function.

The handpiece may be designed in such a case in a way that the actuator element includes a magnet producing a magnetic field which varies in response to the operation of the actuator element at the switch site, and that the switch is closed or opened in response to the magnetic field.

It is moreover expedient to provide the switching means with an actuator element which can be used not only to perform the switching functions but also to vary characteristics of a switching circuit. Due to this feature several functions may be varied via the actuator element. These functions are, for instance, the amplitude, flushing start or stop, suction pressure variations, etc.

To this end the circuit may include resonant circuits with different resonant frequencies; each operation of the actuator element activates at least one resonant circuit. In this embodiment a circuit is provided outside the case or integrated into the case wall, which communicates the commands into the interior of the case by induction. Elements such as induction-coils may be disposed outside or in the case wall and inside the case. With such an arrangement the outer coil becomes part of a resonant circuit when it is connected in parallel with various capacitors via button contacts. This design provides for a characteristic resonant frequency for each function desired. The inner coil serves as sensor for the resonant frequency of the resonant circuit. A circuit detects this frequency and transmits the respective command.

In the aforedescribed embodiment it is sufficient to provide only two signal lines in the lead-in cable of the handpiece. The two lines may be used, for instance, for the starting function and for temperature control in the handpiece and the coding of the handpiece type. To this end diodes are used, for example, to set up a network for interrogation of the reed switch in the current direction and of the temperature via a thermostat switch in the opposite direction. The coding is determined by additional elements such as a resistor connected in series with the thermostat.

To ensure a sufficient safety of the surgeon and the patient in normal operation or in the event of a handpiece defect a sufficient isolation is necessary:

An air gap of 16 mm and a leak path of 23 mm are required by standard for the isolation of 5000 Vpp.

In accordance with the invention the isolation between the high-frequency and the ultrasonic supplies is therefore located in the handpiece, or the ultrasonic generator presents an isolated design.

For isolation between the high-frequency and the ultrasonic supplies in the handpiece possible leak paths can be extended with polyimide strip and/or ceramic and/or silicone and/or GRP and/or CRP materials in particular. This does not take a substantial influence on the ultrasonic function. When silicone is used transverse oscillations are expediently attenuated at the same time, with an improvement of the means preventing torsion.

In another embodiment the isolation is ensured at least partly by means of a heatshrinkable tube (polyvinylidene fluoride (PVDF), silicone, etc.) and/or an isolating ring.

In a further preferred embodiment the case of the handpiece consists of synthetic material. Plastic material offers advantages such as a sound isolation at a low weight.

PEEK material, for instance, comes into question as synthetic material. This plastic material can be sterilised without any restriction. Another possibility is a plastic compound case which is produced, for instance, by a fibre-winding technique, e.g. of plastic material reinforced with glass, carbon or kevlar. The compound plastic cases are preferably thin-walled designs and hence present a small outside diameter and an even lower weight.

A change-over switch is expediently provided—e.g. on the handpiece or between the handpiece and a pumping unit—which when actuated induces an interchange of the function of the suction and flushing lines. As a matter of fact, in a surgical operation it may be expedient to use the flushing passage for suction, e.g. when the suction passage is used as instrument duct. When the suction line is clogged it may be remedial, too, to interchange the flushing with the suction line during a short period in the course of the operation. When the suction line is used for flushing moreover an oriented jet is achieved with a multiplied range (specifically over roughly 30 cm) and a partly fine atomisation when the ultrasonic function is operative at the same time.

To ensure a reliable function the invention moreover provides for the arrangement of mounts, holders or couplers of tubes, pipes, electrical connectors and/or seals in the vicinity of nodal points (spacing less than λ/8) or in nodal points. This provision reduces the dissipation, the fatigue and the heating of the parts to a minimum. As examples of such a design the suction tube in the terminal, the flushing tube in the bolt, the ceramic suspension in the envelope, the supports on the terminal and on the extended probe, the welding site of the piezo elements near the node as well as the high-frequency connector near the node should be mentioned here.

The terminal of a sonotrode is commonly trimmed at the tip until it vibrates at the proper frequency. In such an approach, however, the terminal does not present a defined length and can therefore not always be combined with an envelope of a defined length, which surrounds the terminal. With a precisely defined length of the terminal it is not necessary to match the envelope with the terminal. The resonant frequency is increased, for instance, by truing the outer diameter at the coupling site, i.e. at an antinode, which induces a reduction of the oscillating mass. The frequency becomes lower when truing is performed at a node as the elasticity constant is reduced in this manner.

For certain surgical techniques (e.g. resection of the prostate) which require an efficient removal of tissue with a combination of ultrasound and supply of high-frequency energy it is moreover expedient to dispose a removal-enforcing element in the zone of the distal sonotrode end (near the patient). This element may be an annular envelope, for instance, which presents the design of a cutting loop ring. The annular envelope may also be mounted on a probe without a bore.

On account of the high acceleration at the tip a highly rigid design is desirable. The generatrix of the annular envelope or the loop ring, respectively, expediently follows an exponential or square curve. Specifically wire loops having a constant cross-section are not sufficiently efficient for ultrasonic transmission due to their inertia and yield.

With a parallel orientation of the mid-vertical of the annular envelope and the axis of symmetry of the sonotrode a high rigidity is achieved and hence a high removal rate may be obtained.

The annular envelope is expediently welded to the sonotrode.

For a prolongation of the service life of the probe or an increase of its endurance the tip of the sonotrode and/or the annular envelope is expediently subjected to surface treatment or made of hard metal. Such a tip is particularly well suited for the removal of hard concretions. Furthermore, a hard-metal insert may be fastened by soldering or welding.

Moreover, a suction line is expediently used which is straight. The straight extension allows for the use of the suction line as instrument duct and/or the introduction of an optical examination system and/or a light guide for laser treatment.

In a multi-functional surgical instrument according to prior art a conduction of the high-frequency high voltage applied to the probe into the ultrasonic generator, due to capacitance between the conductors, may occur so that the generator is destroyed.

This may happen all the earlier the closer the high-frequency lines are to the ultrasonic lines. Flash-over or coupling of the high-frequency cannot be prevented in a multi-functional surgical Handpiece according to prior art, which comprises only a single handpiece for all the envisaged functions.

In accordance with the invention it has now been found that the high-frequency signal components of more than 100 kHz (ranges sensible here: ultra-sound with 18–100 kHz, high-frequency with 100 kHz to 5 MHz) can be coupled out.

The invention is preferably implemented in a multi-functional instrument for endoscopic surgery, which comprises an ultrasonic function for tissue crushing, a high-frequency function for additional cutting and/or coagulation, and a flushing and/or suction function. The functions are controlled by the user by means of an inventive handpiece; either tissue is colliquated or comminuted or sucked-in and torn off in the area of the orifice.

The term "tissue crushing" is to be understood here in the sense that tissue is colliquated or comminuted and sucked in and torn off in the zone of the orifice. Volume or material is removed. The inventive handpiece can therefore also be used indirectly for cutting with a cutting gap of 4 mm. The annular envelope cuts without volume removal. It is used for scraping/planing.

It is furthermore preferred that de-coupling be achieved by means of at least one inductive element and particularly by means of a bucking coil. This offers the advantage that the used lines may, for instance, be wound together about the core of the bucking coil so that their magnetic fields will be compensated in the core. The coil suppresses the "common-mode" high frequency and does not produce any effects on the differential ultrasonic currents.

The live cables between the ultrasonic generator and the bucking coil are expediently discharged to ground by means of capacitive elements. The high-frequency voltage drop takes place in the bucking coil.

BRIEF DESCRIPTION OF THE DRAWING

The invention will be described in the following, without any restriction of the general inventive idea, by exemplary embodiments, with reference to the drawing to which explicit reference is made in all other respects as far as the disclosure of all details is concerned which are not explained more thoroughly in the text. In the drawing:

FIG. 3: shows a cross-sectional view taken through another part of a handpiece;

FIG. 4: like FIG. 3, only with another embodiment,

DESCRIPTION OF EMBODIMENTS

Figure 1:
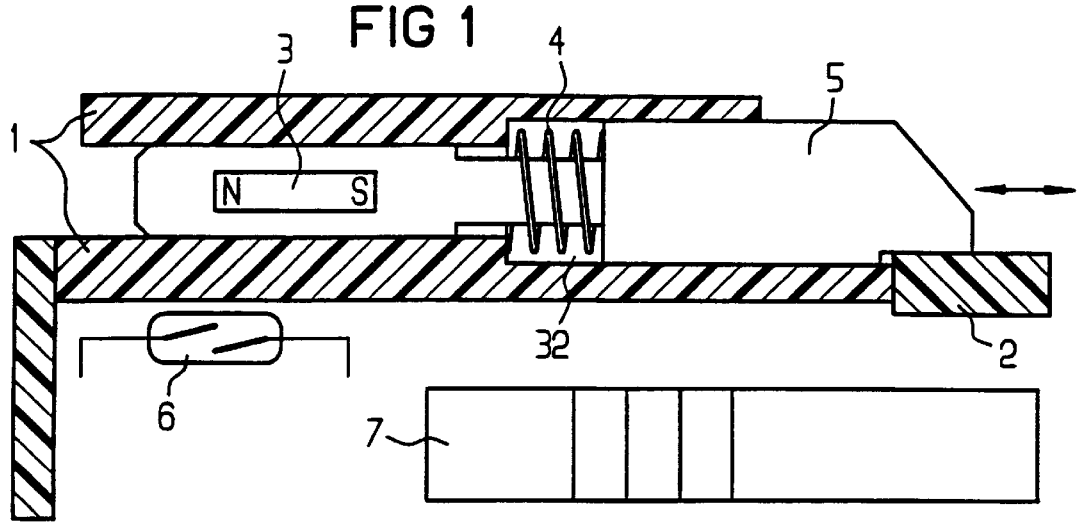
FIG. 1: shows part of a handpiece in a schematic view, representing the actuator element and the piezo element.
Figure 2:
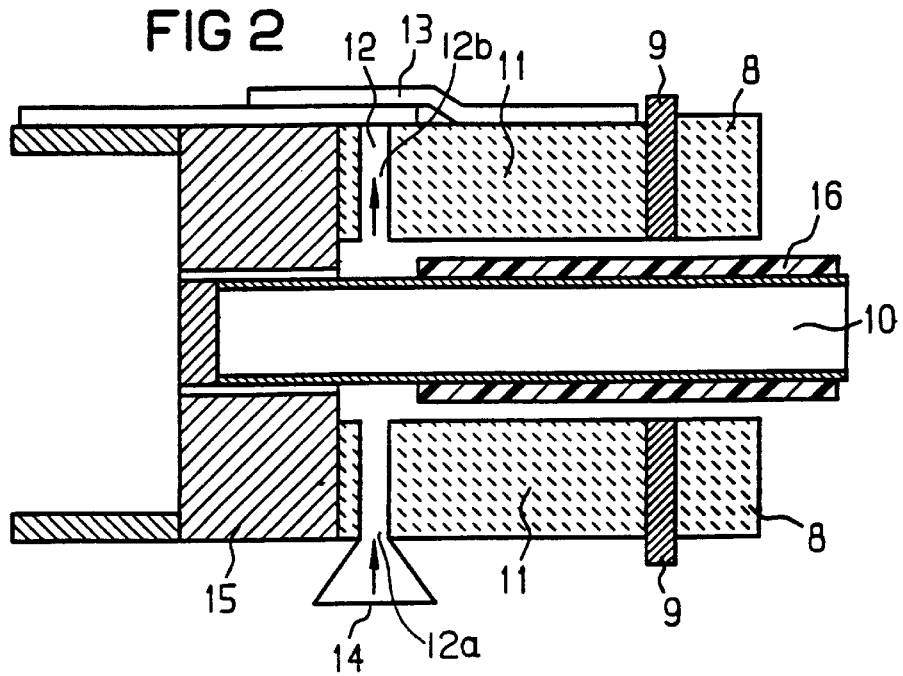
FIG. 2: is a cross-sectional view taken through one part of a handpiece.

In the following figures the same reference numerals denote respectively equal or corresponding parts so that a repeated description will be dispensed with and merely the variations of the embodiments illustrates in these figures from the previous embodiments will be explained.

FIG. 1 is a schematic cross-sectional view of one part of an inventive handpiece. This Figure serves to explain specifically the switching function by remote operation.

The reference numeral 1 denotes the rear case part and numeral 2 identifies the front case part. A reed relay 6 or a reed contact 6, respectively are switched by means of a permanent magnet 3 which is connected to a slide 5, in this case the actuator element, by displacement of the slide 5 and hence the magnet 3. A spring 4, which is inserted into an offset bore 32, like the slide 5, serves to push the slide again into its initial position. The slide 5 presents a milled tip so that it is protected from falling out by the front case part 2. The double arrow indicates the movement of the slide 5. Only when the slide 5 is operated, for instance, the ultrasonic voltage is applied to the end of the handpiece. When the case is dismantled the slide can be removed for cleaning. FIG. 1 moreover shows piezo elements 7.

FIGS. 2 to 5 roughly illustrate various possibilities of isolation between the ultrasonic section and the high frequency section. In operation it is necessary—particularly in the event of a defect and also in normal operation—to provide an electrical insulation of the high frequency from the ultra-sound. In accordance with the invention a bucking coil is used in this embodiment. For this reason, and on account of the capacitive coupling between high frequency and ultra-sound by the used cable accommodating all the lines, the voltage across the insulation in the handpiece amounts only to a fraction of the full high frequency voltage in normal cases. Insulating provisions must be provided between the mains supply and the patient in a magnitude which is derived from the maximum voltage applied. The standards demand an air gap of 16 mm and a leak path of 23 mm for the isolation of 5000 Vpp. This is difficult to implement in the generator so that the insulation provisions are shifted to the handpiece. On the condition that the insulation is implemented in the ultrasonic generator the isolator in the handpiece fulfils the function of additional safety measures.

Specific structures are provided to extend the leak paths between the high frequency and ultrasonic sections, without taking a substantial influence on the ultrasonic function. A tensioning screw 15 with an extension lip is provided on the rear end of the converter or transducer, which is outlined by the piezo section 8 and the electrode 9 in FIG. 2, onto which lip an isolating tape 13 is wound. The tensioning screw 15 with its bolt 10 or the cylindrical edge of the bolt, respectively, are connected to high frequency. An additional isolation is achieved via a ceramic section 11 and a silicone mass 14. To this end a silicone casting substance 14 is pressed along the extension of the arrow through a charging opening 12a until it is discharged at the vent 12b.

The suspension is made, for instance, of an insulating ceramic material 17 (cf. FIG. 3). The space between the front part 2 and the case wall 19 is filled with silicone 14 to achieve a discontinuity of the leak path. This provision serves at the same time to attenuate transverse oscillations and to ensure protection from torsion. The bolt 10 and the piezo sections 8 are insulated by a silicone tube 16. The ends of the tube 16 are cast together with the respective ceramic parts 11 or 17, respectively. Casting is performed through appropriate injection and venting openings 12a and 12b. The silicone casting substance 14 establishes a perfect vulcanisation-type connection with the tube 16. The case wall 19 may be made of plastic material, for instance.

Figure 5:
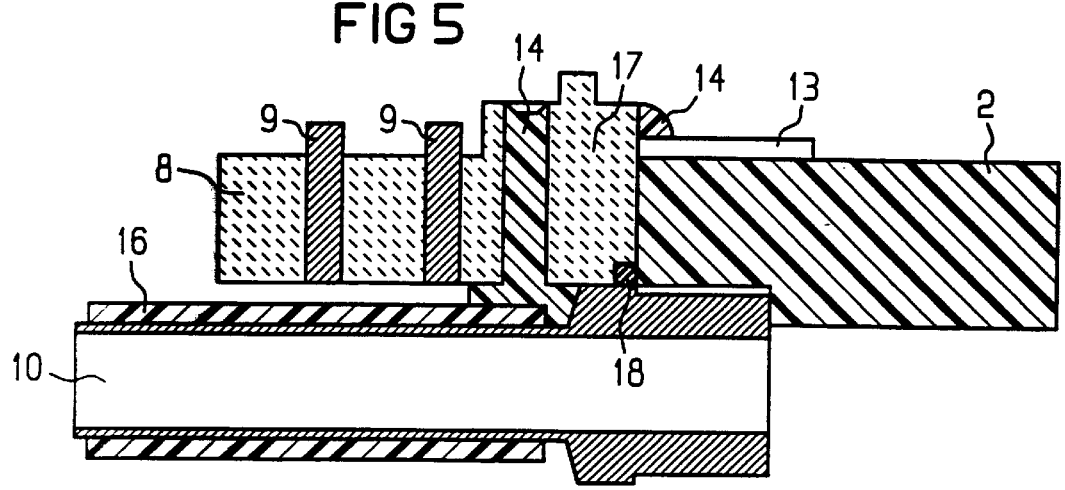
FIG. 5: like FIGS. 3 and 4, with other embodiments.

Another possibility of insulation on the suspension is illustrated in FIG. 4. There the leak path is extended by an isolation ring 20. FIG. 5 illustrates another possibility of isolation. There the front part 2 is wrapped with an insulating tape 13. The site of joint on the ceramic suspension 17 is then sealed with the silicone mass 14.

Figure 6:
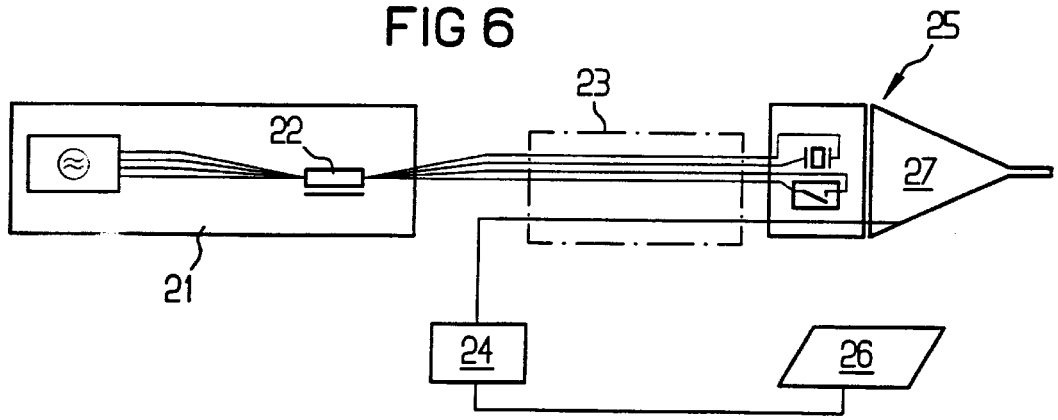
FIG. 6: is a general rough illustration of an inventive surgical instrument with a bucking coil.

FIG. 6 is a schematic view of a multifunctional instrument for endoscopic surgery. The ultrasonic voltage generator 21 comprises a bucking coil 22. The lines from the ultrasonic voltage generator 21 as well as the line from the high frequency generator 24 are passed through a common cable 23 to the handpiece 25. The piezo converter, the reed relay and the sonotrode 27 are schematically indicated in the handpiece 25. Moreover, a neutral electrode 26 is shown in FIG. 6.

The electrical connections (switching lines, high frequency, ultra-sound), which are integrated into a common cable 23, are spliced at the proximal end, specifically into one segment with ultrasonic and switching lines for the ultrasonic voltage generator and one part with the high frequency line for the high frequency generator.

The four lines (here: 2 ultra-sound lines and 2 signal lines) are wound about the core of the bucking coil 22 such that the coil will suppress the "common-mode" high frequency component and will not take an influence on the differential ultrasonic and signal currents.

Figure 7:
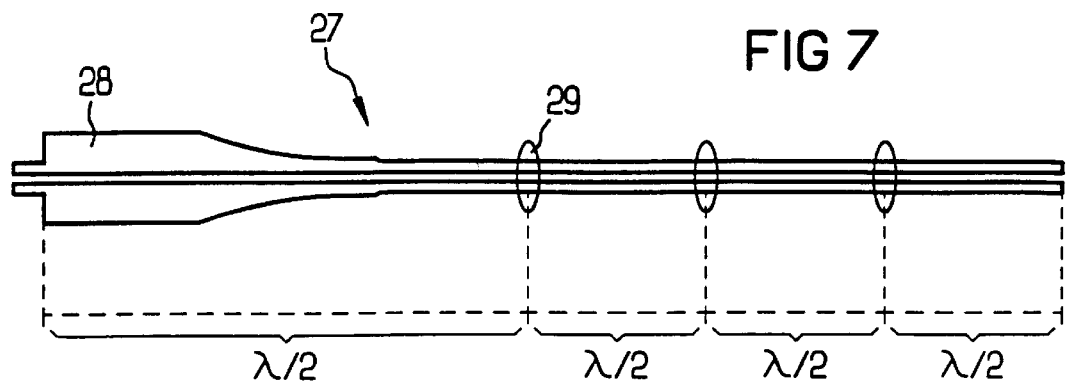
FIG. 7: shows a sonotrode having a length of $4*\lambda/2$.

The inventive handpiece is particularly well suitable for application with trocars using sonotrodes having an extended length. This becomes evident from FIG. 7 in particular which shows a sonotrode 27. The reference numeral 28 in FIG. 7 indicates a screw thread for fastening the sonotrode on the handpiece case so as to establish specifically the coupling with the piezo elements. The sonotrode as illustrated presents a length of four half-wave lengths. The weld sites are provided in the anti-nodal points 29 of the half-wave lengths. The sonotrode of FIG. 7 presents an anti-nodal point at the end close to the patient.

The welding sites are necessary because the titanium alloys used are not available in the form of the appropriate tube so that the probes must be deeply bored. Extended probes such as those used in endoscopic applications, e.g. for insertion into trocars, are composed of various segments because deep boring is possible only up to 200 mm at a reasonable reject rate (20%). It has been found according to the invention that the desired ultrasonic characteristics and the endurance can be achieved with little to no subsequent finishing by welding. Moreover, the welding technique is inexpensive and reliable, which means that the number of rejects is low.

Figure 8:
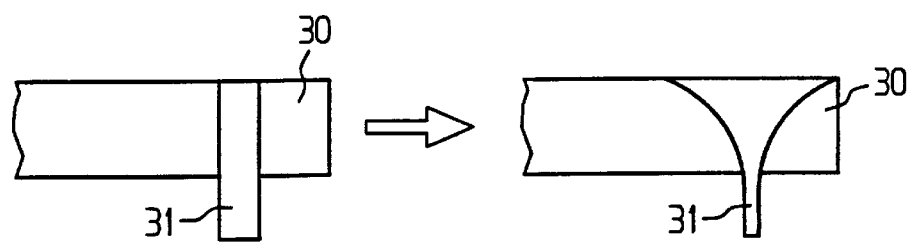
FIG. 8: illustrates the tip of the probe with an annular envelope (on the left side with a cylindrical design and on the right side with an exponential design)
Figure 9:
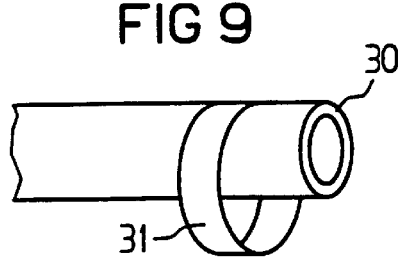
FIG. 9: is a perspective view of the probe tip with the annular envelope in a cylindrical design.

In order to achieve an efficient tissue removal with certain surgical techniques (resection of the prostate) the invention provides for the arrangement of an annular envelope at the probe tip. FIG. 8 shows a side view of a probe tip 30 with an annular envelope 31 for such applications. On the left side, a cylindrical design is illustrated which is shown again in a perspective view in FIG. 9. The right side of FIG. 8 illustrates an annular envelope 31 having an increased rigidity due to an exponential curve of the shape. An increased rigidity is required in view of the very high acceleration and hence the high load on the material in ultrasonic applications.

LIST OF REFERENCE NUMERALS 1 rear case part
2 front case part
3 magnet
4 spring
5 slide
6 reed contact
7 piezo elements
8 piezo sections
9 electrode
10 bolt
11 ceramic section 12 vent
13 captone section
14 silicone mass
15 tensioning screw
16 silicone tube
17 ceramic suspension
18 O-ring
19 plastic case wall
20 isolation ring
21 ultrasonic voltage generator
22 bucking coil
23 cable
24 high-frequency generator
25 handpiece
26 patient-contact electrode
27 sonotrode
28 screw thread
29 nodal point
30 probe tip
31 annular envelope
32 offset bore

What is claimed is:

1. Handpiece for a multifunctional instrument for endoscopic surgery, comprising
   a case,
   a connector disposed on the case and adapted to receive lines,
   at least one ultrasonic transducer arranged in said case,
   an ultrasonic sonotrode for transmitting an ultrasonic wave from said transducer, and
   at least one switch disposed within the handpiece for controlling functions of the handpiece,
      characterized in that said sonotrode includes a long and thin probe section with a duct composed of several segments welded to each other, and
      further characterized in that said switch comprises at least one sensor and an associated switching circuit as well as at least one actuator element, and that said at least one actuator element does not include any part which may be brought into direct mechanical contact with the respective sensor.

2. Handpiece according to claim 1, characterized in that the welding sites are located in anti-nodal points of the ultrasonic wave.

3. Handpiece according to claim 1, characterized in that at least the probe section includes titanium, and that the diameter of the duct amounts to roughly 2 mm, the thickness of the probe section is less than 4 mm, and the length is more that 30 cm.

4. Handpiece according to claim 1, characterized in that said sonotrode presents a bulge on its proximal side, which is welded to the probe section and screwed to the case.

5. Handpiece according to claim 1, characterized in that said connector is adapted to receive lines selected from the group comprising electrical lines, discharge lines, liquid supply lines and combinations of these.

6. Handpiece according to claim 1, characterized in that said switching circuit operates in a manner selected from the group comprising magnetically, by induction, electromagnetically, optically, acoustically, and combinations of these.

7. Handpiece according to claim 6, characterized in that said actuator element comprises a magnet generating a magnetic field which varies at said sensor by operation of said actuator element, and that said sensor is closed or opened in response to this magnetic field.

8. Handpiece according to claim 6, characterized in that said sensor is selected from the group comprising a reed relay and a Hall probe.

9. Handpiece according to claim 1, characterized in that said switch controls at least one switching circuit.

10. Handpiece according to claim 8, characterized in that said at least one actuator element comprise resonant circuits with different resonant frequencies, and that the operation of said at least one actuator element activates at least one resonant circuit.

11. Handpiece according to claim 9, characterized in that a coil and a circuit are provided in the handpiece for inductive detection of a resonant frequency of an activated resonant circuit.

12. Handpiece according to claim 1, characterized in that only two signal lines for a starting function as well as further functions are provided.

13. Handpiece according to claim 1, characterized in that additionally a high-frequency generator is provided.

14. Handpiece according to claim 13, characterized in that possible leak paths are extended or rendered discontinuous for isolation between the high-frequency supply and an ultra-sound supply in the handpiece.

15. Handpiece according to claim 14, characterized in that the isolation is implemented with a device selected from the group comprising a PVDF tube and an isolation ring.

16. Handpiece according to claim 14, characterized in that said case is comprised of synthetic material.

17. Handpiece according to claim 1, characterized in that the duct in said sonotrode extends along a straight line through the handpiece up to a fluid port.

18. Handpiece according to claim 17,
   characterised in that the duct serves for suction or flushing.

19. Handpiece according to claim 18,
   characterised in that a change-over switch is provided which may be actuated for changing operation from suction over to flushing and vice versa.

20. Handpiece according to claim 1, characterized in that couplers are mounted to said duct at a distance from nodal points of less than $\lambda/8$.

21. Handpiece according to claim 1, characterized in that a removal-intensifying element is provided near a distal end of said sonotrode.

22. Handpiece according to claim 21,
   characterised in that said removal-intensifying element is a cutting loop ring.

23. Handpiece according to claim 22, characterized in that a vertical axis of symmetry of said cutting loop ring and an axis of symmetry of the sonotrode are arranged in parallel.

24. Handpiece according to claim 22, characterized in that said cutting loop ring is wider at an end adjacent the sonotrode than at an end remote from the sonotrode.

25. Handpiece according to claim 24, characterized in that said loop ring has a contour which follows an exponential or square curve.

26. Handpiece according to claim 22, characterized in that said loop ring is welded to the sonotrode.

27. Handpiece according to claim 22, characterized in that hard metal is used to form a tip of the sonotrode and a blade of said loop ring.

28. Handpiece according to claim 17, characterized in that a suction line is further provided.

29. Handpiece according to claim 1, characterized in that high-frequency signal components are coupled out before reaching an ultrasonic generator providing the voltage supply for the ultrasonic function.

30. Handpiece according to claim 29, characterized in that the ultrasonic generator comprises at least one inductive element and further characterized in that the high-frequency signal components are coupled out by the at least one inductive element.

31. Handpiece according to claim 30, characterized in that a bucking coil serves as the inductive element.

32. Handpiece according to claim 31, characterized in that live cables of the ultrasonic generator are wound around the core of said bucking coil so that their magnetic fields are compensated in the core.

33. Handpiece according to claim 30, characterized in that live cables of the ultrasonic generator are attenuated towards ground by capacitive elements.

34. Handpiece according to claim 1, characterized in that said ultrasonic transducer is composed of piezo disks.

35. Handpiece according to claim 34, characterized in that the ultrasonic transducer comprises an inertial mass and further characterized in that the number of said piezo disks is odd, and that said piezo disks are isolated from the inertial mass.

36. Handpiece according to claim 34, characterized in that an ultrasonic generator is provided for controlling said ultrasonic transducers and further characterized in that the ultrasonic generator has a floating symmetrical output.

* * * * *